United States Patent [19]
Taylor

[11] Patent Number: 5,277,698
[45] Date of Patent: Jan. 11, 1994

[54] KNEE BRACING METHOD

[75] Inventor: Dean A. Taylor, Vancouver, Canada

[73] Assignee: Generation II Orthotics, Inc., British Columbia, Canada

[21] Appl. No.: 934,819

[22] Filed: Aug. 24, 1992

Related U.S. Application Data

[63] Continuation-in-part of Ser. No. 697,146, May 8, 1991, abandoned.

[51] Int. Cl.$^5$ .............................................. A61F 5/00
[52] U.S. Cl. ...................................... 602/26; 602/16
[58] Field of Search ............................... 602/26, 16, 23

[56] References Cited

U.S. PATENT DOCUMENTS 4,632,098 12/1986 Grundei et al. .
4,821,707 4/1989 Audette .
5,002,045 3/1991 Spademan .

FOREIGN PATENT DOCUMENTS 2136294A 9/1984 United Kingdom .

Primary Examiner—Richard J. Apley
Assistant Examiner—Lynne A. Reichard
Attorney, Agent, or Firm—Townsend and Townsend Khourie and Crew

[57] ABSTRACT

A method of reducing the effect of unicompartmental osteoarthritis of a knee. A force is applied to the knee on that side of the knee remote from the compartment having osteoarthritis as the knee moves to extension. Preferably, the force is applied at a point about 10° to 15° posterior of the normal axis of rotation of the knee.

7 Claims, 5 Drawing Sheets

KNEE BRACING METHOD

This is a continuation-in-part of application Ser. No. 07/697,146 filed May 8, 1991 now abandoned.

FIELD OF THE INVENTION

This invention relates to a method of reducing the effect of unicompartmental osteoarthritis in a knee joint.

BACKGROUND OF THE INVENTION

The knee joins the femur to the tibia and is controlled by ligaments and cartilage. Contact between the femur and the tibia occurs across the cartilage and there are so called compartments or spaces at each side of the knee. The medial compartment is on the inside of the knee, the lateral compartment is on the outside of the knee.

Unicompartmental osteoarthritis, which may occur in the medial compartment or in the lateral compartment, is a mechanical malfunction of the knee whereby uneven distribution of pressure occurs across the knee causing excessive wear on the inside of the knee joint in medial compartment osteoarthritis and on the outside of the knee joint in lateral osteoarthritis.

Unicompartmental medial osteoarthritis is most common in men. The male pelvis is somewhat narrower than the female pelvis and a male's legs tend to be varus, that is males have a greater tendency to bow-leggedness. Unicompartmental lateral osteoarthritis is most prevalent in females due to the wider pelvis of the female and the fact that the legs are more often in valgus (that is females tend to be knocked-kneed).

A healthy knee joint has an even distribution of pressure medially and laterally and the space between the femur and tibia is approximately one quarter inch.

Unicompartmental osteoarthritis can be induced by injury or by aging. With the advancement of the disease, the space between the femur and tibia decreases. The problem may progress to the extent that the space is eliminated and the femur contacts the tibia. In those circumstances, erosion of the tibia may result.

With the disease there is a change in the normal angle between the femur and tibia. For example, if the patient normally stands in 2° of varus, that is bowleggedness, then with the advancement of the disease, the angle will increase to, for example, about 5° of varus.

Lateral thrust upon heel strike often accompanies the increase in the mis-alignment of the femur and the tibia. This tends to stretch the ligaments on the opposite side as well as having an adverse effect on the knee joint, tending to emphasize the erosion of the tibia.

A further complication is that rotational slackness develops as the space between the compartment is reduced. This is caused by slackening of the ligaments as the attachment points of the ligaments move closer together with bone deterioration.

SUMMARY OF THE INVENTION

The present invention seeks to reduce the effects of unicompartmental osteoarthritis, both medial compartment osteoarthritis and lateral compartment osteoarthritis. Accordingly, the present invention provides, a method of reducing the effect of uni-compartment osteoarthritis of a knee that comprises applying a force to the knee on that side of the knee remote from the compartment having osteoarthritis as the knee moves to extension.

In a preferred aspect the force is applied at a point 10° to 15° posterior from the normal axis of rotation of the knee.

In a particularly preferred embodiment the force is applied by a brace that includes a cross strap tightenable across the knee and providing the means of applying the force. The brace includes a hinge mechanism.

BRIEF DESCRIPTION OF THE DRAWINGS

Aspects of the invention are illustrated, merely by way of example, in the accompanying drawings in which.

DESCRIPTION OF THE PREFERRED EMBODIMENT

Figure 1:
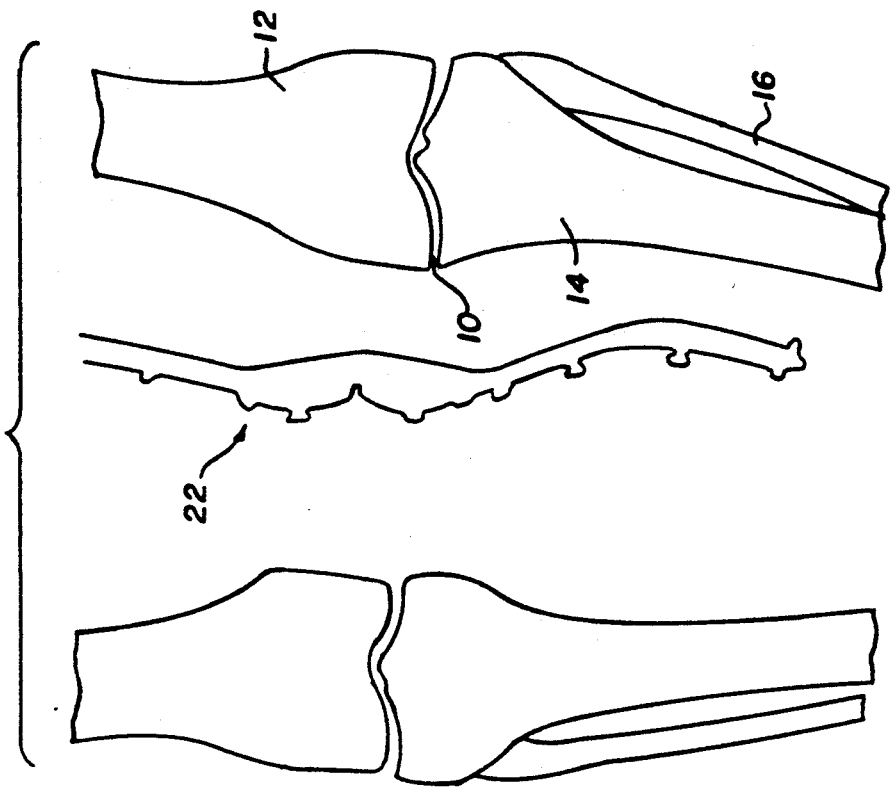
FIG. 1 is an X-ray view, taken from the front, of the legs of a male afflicted with osteoarthritis in the left leg.
Figure 2:
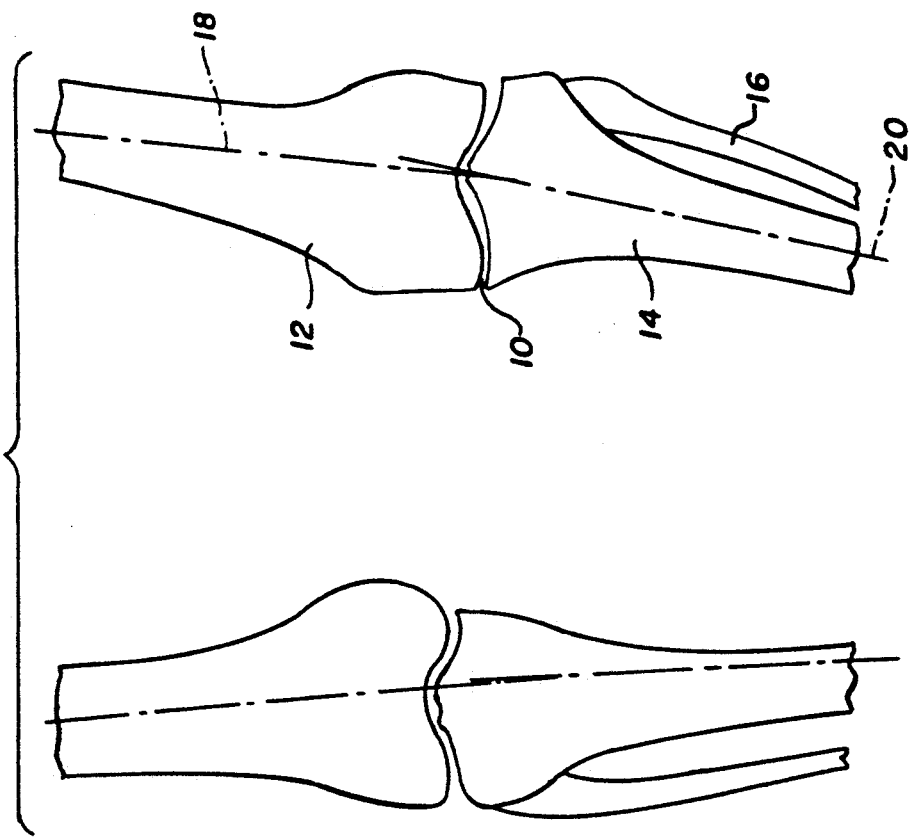
FIG. 2 is a view showing the correction of the problem by a brace in accordance with the invention.

FIGS. 1 and 2 of the drawings are representations of X-ray photographs of the knees of a male. As shown particularly in FIG. 2 the male has a healthy right knee, but the medial compartment 10 of the left leg is decreasing in height so that the femur 12 is closer to the tibia 14. For the purpose of illustration, the fibula 16 is also shown. The effect of the collapse of compartment 10 is shown by the axial lines 18 and 20.

FIG. 2 shows the medial compartment opened slightly by the wearing of a brace 22 on the left knee. The brace is shown in more detail in FIGS. 3 and 4. Only X-ray opaque components of brace 22 are shown in FIG. 2.

Figure 3:
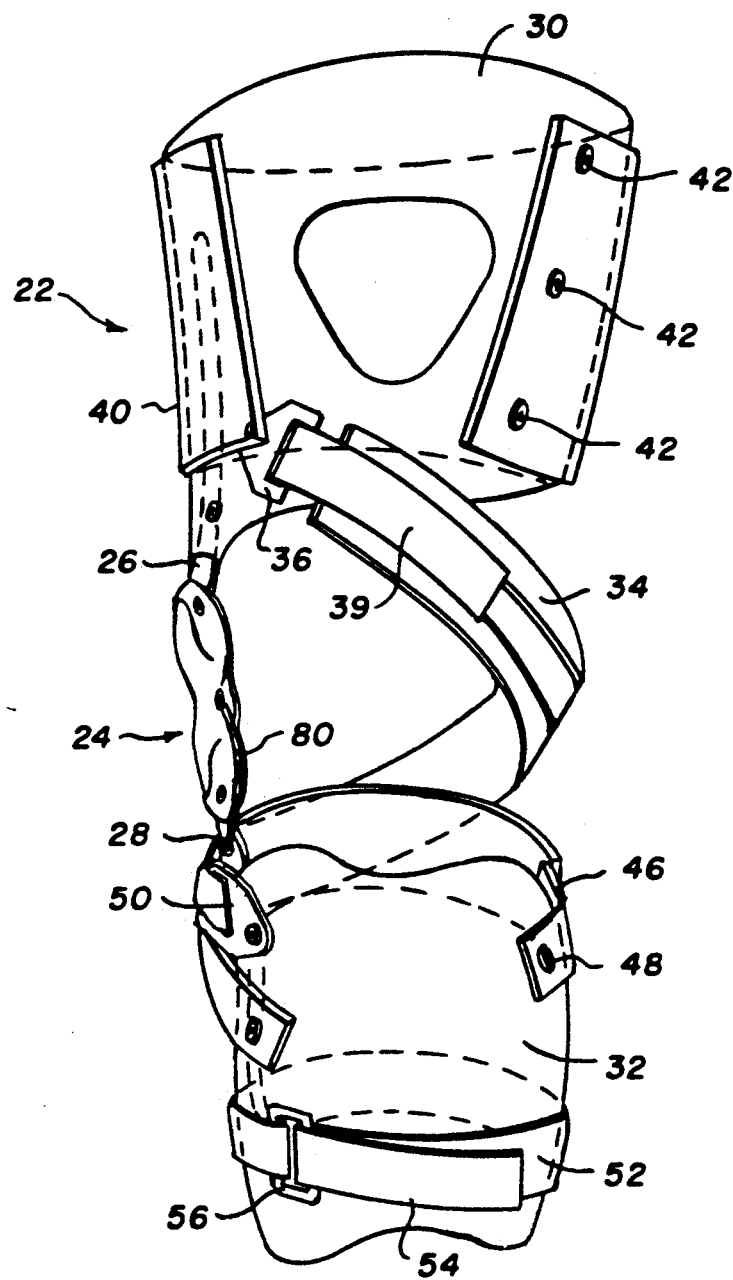
FIG. 3 is a front view of a brace used in accordance with the present invention.

Referring to FIG. 3, the brace 22, as used in FIG. 2, is seen to include a hinge 24 having rigid limbs 26 and 28 extending from it. Limb 26 is attached to an upper cuff 30 and limb 28 is attached to a lower cuff 32. The upper cuff 30 is located above the knee and the lower cuff 32 below the knee. The hinge 24 joining the cuff is adjacent the knee and, more particularly, adjacent the compartment with osteoarthritis.

There is across strap 34 pivotally anchored to the upper cuff at bracket 36 and able to extend around the knee to a pivotal connection to the lower cuff at 32. Bracket 36 has an opening through which cross strap 34 can extend. The strap 34 is provided with hook and pile fasteners 39 because of the wide range of adjustments possible with these fasteners. The strap 34 is led through the bracket 36, back on itself to be fastened to itself by the hook and pile fastener. There is preferably a soft foam plastic cuff attached to the cross strap 34 to make contact with the wearer.

The upper cuff 30 also includes a thigh strap 40 extending from anchor points 42 and, again, having a hook or pile fastener at one end to mate with a pile or hook anchor point on the upper cuff 30. In this way, the upper cuff 30 can be securely attached to the thigh of a wearer. Beneath the knee, the lower cuff 32 is attached by an upper strap 46, extending from a pivotal anchor point 48 round through an attachment bracket 50 and back on itself, again using hook and pile fasteners. In this way, again by threading the strap through the bracket 50, the lower cuff 32 can be secured immediately beneath the knee of the wearer.

There is a second lower strap 52 on the lower cuff 32 to attach the cuff around the calf of the wearer. Again, the preferred form of attaching is by hook and pile pieces 54 positioned on strap 52 with the strap able to extend through a bracket 56, back on itself.

Figure 4:
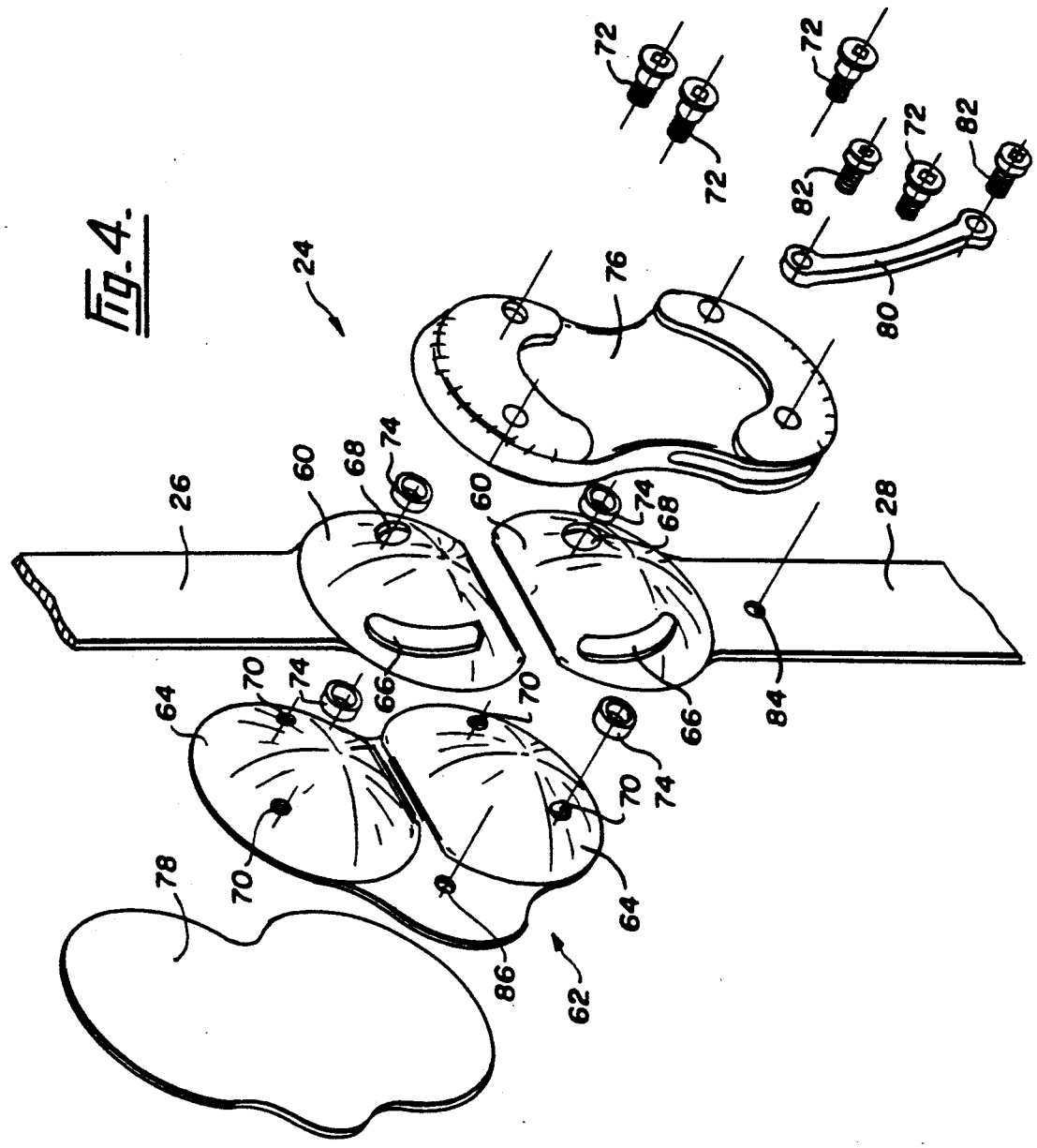
FIG. 4 is a detail of the brace of FIG. 3.

As shown particularly in FIG. 4, the hinge 24 of the brace comprises an upper limb 26 and a lower limb 28. At the end of each limb there is a part spherical body 60. There is a connector piece 62 comprising a pair of part spherical bodies 64, one such part spherical body to be received in each part spherical body 60 of the limbs 26 and 28. There are openings 66 and 68 formed in the bodies 60 and threaded openings 70 formed in the connector piece 62. Threaded members 72 extend through the bodies 60 to engage in the connector piece 62. At the front of the brace, that is the part of the brace closer to the knee cap, the openings 66 are elongated. There are nylon or the like bushes 74 located in the openings in the hinge piece spherical bodies 60 to facilitate the necessary rotational movement. The elongated front openings 66 guide and restrict the amount of movement available.

This arrangement of part spherical bodies 60 and 64 has been found to be ideal in duplicating the complicated movement of the knee where the pivotal axis changes with movement of the knee.

There is a cover piece 76, through which the threaded members 72 extend and an inner contact member 78, where the hinge contacts the knee of the wearer. In addition, there is an elastic member 80, for example of polyurethane, which is anchored by anchoring bolts 82 at opening 84 in the lower limb 28 and opening 86 in the connector piece 62. Member 80 tends to urge the brace from the flexed to the extended position to assist a weakened knee.

In operation, the brace is attached to the wearer, for whom it will usually be custom made, by attaching the upper cuff 30 and lower cuff 32, using straps 40, 46 and 52. The hinge 24 is located against the knee having compartment osteoarthritis. In a male, typically the hinge will be on the inside of the knee; for a female the hinge will usually be on the outside of the knee.

The cross strap 34 is then led around the knee, through the bracket 36 and round back on itself to be fastened. This arrangement ensures that the cross strap 34 tightens as the leg moves into extension and loosens as the leg moves into flexion. This tightening of the strap 34 during the extension of the knee prevents the lateral movement of the bone upon extension of the leg, that is prevents the adverse effect of compartment osteoarthritis. Tightening is achieved by the fastening points of the cross strap becoming further apart as the leg moves into extension. Further, the hinge tends to flatten as it moves from flexion to extension which also tends to tighten the strap 34 around the leg.

The tightening of the cross strap 34, in combination with the rigidity and strength of the hinge 24, tends to de-pressurize the compartment to increase the space between the two bones on the affected side of the knee. The hinge is placed externally and rotates at approximately 15°. This positioning allows the hinge 24 to go into valgus or varus when it moves from extension to flexion depending on how the brace has been fitted.

The limbs 26 and 28 provide reaction points for the cross-strap 34. Thus tightening of the strap 34 causes limbs 26 and 28 to stabilize the knee on the hinge side, opposite the point of application forced by strap 34. A triangle of forces is created with the strap acting at the triangle apex, urging the knee to the base of the triangle defined by the limbs 26 and 28.

Figure 5:
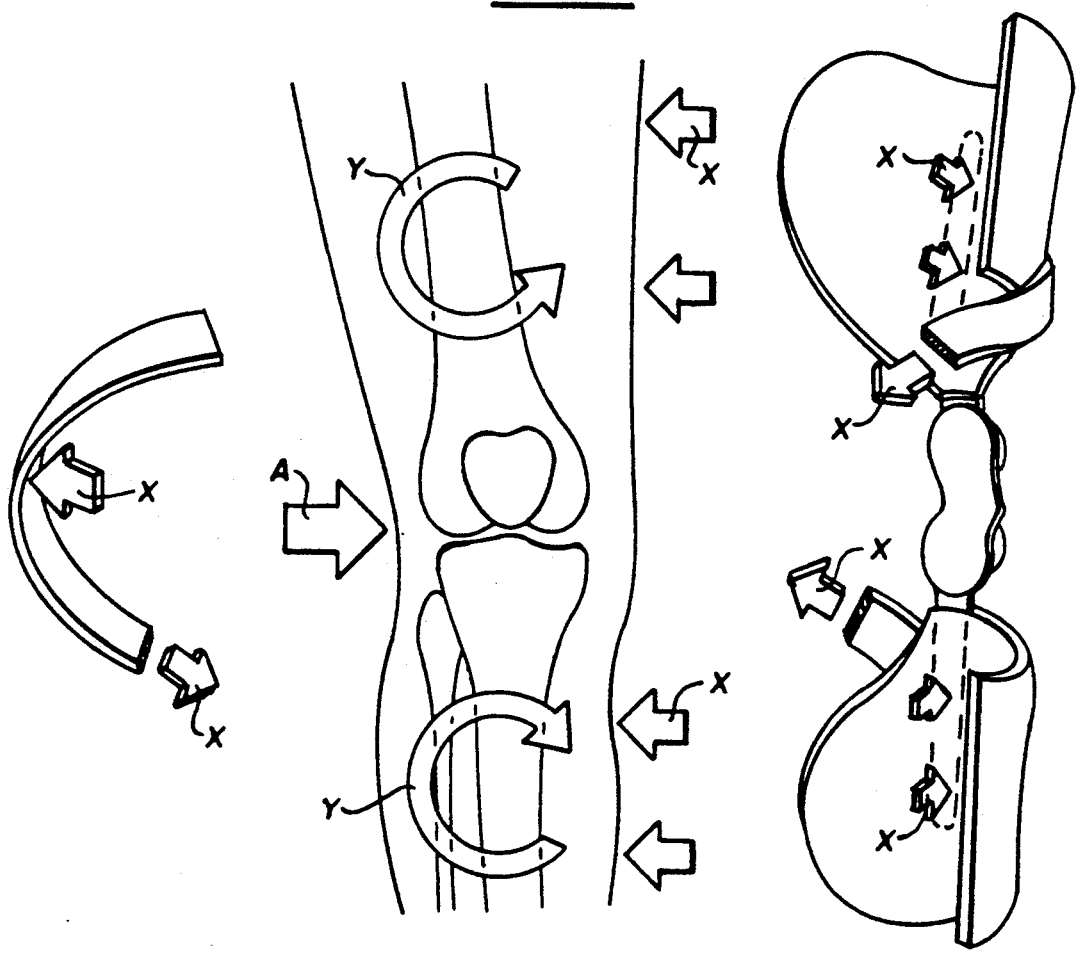
FIG. 5 illustrates the application of force using the brace as shown in FIG. 2.
Figure 6:
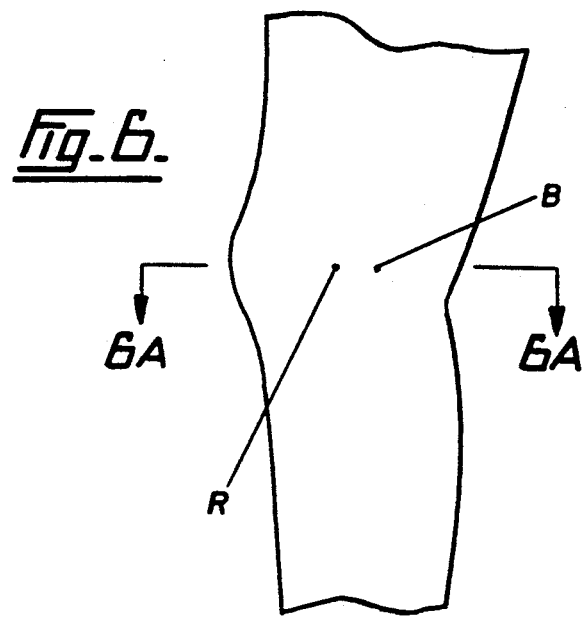
FIG. 6 generally illustrates where the force is applied externally of the knee.
Figure 6A:
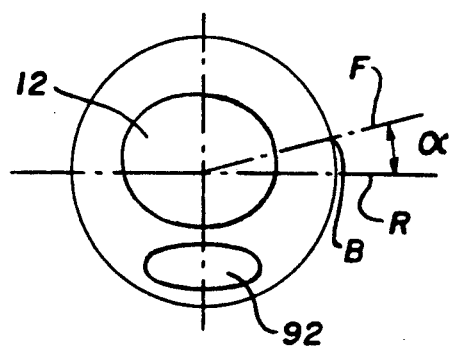
FIG. 6A is a sectional view taken along line 6A—6A of FIG. 6.

FIG. 5 illustrates the application of forces using the brace of FIG. 2. The arrows X show lateral and cross strap forces. The resulting moments in the leg due to lateral forces are shown by the arrows Y. The principal force A is that applied immediately adjacent that compartment of the knee remote from the compartment having osteoarthritis. Referring to FIGS. 6 and 6A, the principal force is applied (as the knee moves to extension) at a point B1 which is about 10° to 15° posterior of the normal axis of rotation R of the knee as designated by reference character $\alpha$ in FIG. 6A, to provide the desired results. Referring to FIG. 6A, the principal force acts along line F which is 10°-15° posterior of rotational axis R of the knee (knee cap 92 being in front of rotational axis R). The positions of the anchor points where strap 34 is anchored to upper cuff 30 and lower cuff 32 determines where the principal force from strap 34 is applied. The configuration illustrated in FIG. 3 provides a principal force that is applied about 10°-15° posterior of the rotational axis of the knee.

The brace thus produces a relatively mild valgus-producing force at the knee throughout the swing phase of gait with an increasing valgus force as the leg moves closer to heel strike when the brace is on the inside of the knee. The maximum force is at full extension as, at that position, the anchor points are furthest apart. The force then decreases as the weight on the leg decreases during the follow through phase, that is flexion of the knee. A patient with medial compartment osteoarthritis tends to walk with the affected leg externally rotated so as to unload or unweight the medial compartment upon heel strike. As a result, these patients significantly alter their gait but are generally unaware that they are doing so. The rotation of the leg tends to be greater below the knee as the relatively slack leg ligaments tend to allow rotation. This is overcome by the cross strap which has a tendency to rotate the tibia internally as the leg moves through the swing phase with the maximum amount of torsion being at full extension when the diagonal strap is at its tightest.

This rotational slack between the tibia and the femur is bi-directional and is controlled in the invention by the inherent torsional rigidity of the brace. The tibia and the femur are, in effect, connected together with a semi-rigid frame and the hinge mechanism allows for normal flexion and extension. Muscle movement limits excessive torsion load between the tibia and the femur.

The present invention thus provides a simple, yet effective method of relieving the effects of unicompartmental osteoarthritis of a knee. It is effective whether worn on the outside of the knee or the inside of the knee.

What is claimed is:

1. A method of reducing the effect of unicompartmental osteoarthritis of a knee of a leg that comprises applying a brace around and against the knee such that the principal force generated by the brace on that side of the knee remote from the compartment having osteoarthritis as the knee moves to extension is applied on that side at a point about 10° to 15° posterior of the normal axis of rotation of the knee.

2. A method as claimed in claim 1 in which said principal force is applied by a brace that includes a hinge having first and second rigid limbs extending from it and a cross strap having first and second ends and being tightenable across the knee to urge the knee towards the hinge on extension of the knee.

3. A method as claimed in claim 2 in which the brace includes upper and lower cuffs to be located one above and one below the knee with the hinge joining the cuffs on that side of the knee adjacent the compartment with osteoarthritis;

the cross strap being anchored to one cuff to extend around the knee, remote from the hinge, then back to a fastening point on the second cuff;

whereby extension of the leg acts to tighten the cross strap to apply a force against the knee and flexion of the leg acts to loosen the cross strap about the knee.

4. A method as claimed in claim 3 in which the brace includes a hinge mechanism comprising part spherical bodies formed one at an end of each limb;

a connector piece comprising a pair of part spherical bodies, one to be received in each part spherical body of the limbs;

openings formed in the part spherical bodies of the limbs;

threaded openings formed in the connector piece;

threaded members to extend through the hinge spherical members to engage in the connector piece;

the spherical arrangements allowing control of movement of the knee and the openings guiding and restricting the amount of movement available.

5. A method as claimed in claim 4 in which the hinge includes an elastic member extending from an anchor point on the connector piece to an anchor point on the lower cuff member whereby the brace is urged from the flexed to the extended position.

6. A method as claimed in claim 1 wherein the brace is applied such that the point at which the principal force is applied and the normal axis of rotation of the knee define a plane that is generally perpendicular to the longitudinal axis of the femur of the leg when the leg is extended.

7. A method as claimed in claim 2 including coupling the first end of the strap to the first rigid limb, coupling the second end of the strap to the second rigid limb, spirally wrapping the cross strap around the knee, and applying the principal force to said point through the cross strap.

* * * * *